US010813980B2

(12) United States Patent
Carelli et al.

(10) Patent No.: US 10,813,980 B2
(45) Date of Patent: Oct. 27, 2020

(54) METHODS FOR TREATING OSTEOARTHRITIS BY ADMINISTERING LINKED VARIANTS OF GROWTH HORMONE AND SOMATOSTATIN

(71) Applicant: REGULAXIS, Romainville (FR)

(72) Inventors: Claude Carelli, Suresnes (FR); Christelle Vêtu, Montreuil (FR); Raffaello Paolini, Paris (FR)

(73) Assignee: REGULAXIS, Romainville (FR)

( * ) Notice: Subject to any disclaimer, the term of this patent is extended or adjusted under 35 U.S.C. 154(b) by 0 days.

(21) Appl. No.: 16/308,520

(22) PCT Filed: Jun. 9, 2017

(86) PCT No.: PCT/EP2017/064196
§ 371 (c)(1),
(2) Date: Dec. 10, 2018

(87) PCT Pub. No.: WO2017/212057
PCT Pub. Date: Dec. 14, 2017

(65) Prior Publication Data
US 2019/0298808 A1    Oct. 3, 2019

(30) Foreign Application Priority Data
Jun. 10, 2016   (EP) .................................... 16174056

(51) Int. Cl.
*A61K 38/27* (2006.01)
*A61P 19/02* (2006.01)
*A61K 38/31* (2006.01)
*A61K 31/728* (2006.01)
*A61K 9/00* (2006.01)

(52) U.S. Cl.
CPC ............ *A61K 38/27* (2013.01); *A61K 31/728* (2013.01); *A61K 38/31* (2013.01); *A61P 19/02* (2018.01); *A61K 9/0019* (2013.01)

(58) Field of Classification Search
CPC ...... A61K 38/27; A61K 38/31; A61K 31/728; A61K 9/0019; A61K 47/36; A61P 19/02; C07K 14/61; C07K 14/655; C07K 2319/00
See application file for complete search history.

(56) References Cited

U.S. PATENT DOCUMENTS

| 2004/0127402 A1 | 7/2004 | Vad |
| 2004/0253723 A1 | 12/2004 | Tachas et al. |
| 2007/0184015 A1 | 8/2007 | Hahn |

FOREIGN PATENT DOCUMENTS

| WO | 03/048206 A2 | 6/2003 |
| WO | 2010/105685 A2 | 9/2010 |

OTHER PUBLICATIONS

Kumar S, et al. (Apr. 22, 2014) J Sci Food Agric. 6 pages. (doi 10.1002/jsfa.6752).*
Nakatani S, et al. (2009) Osteoarthritis and Cartilage. 17:1620-1627. (doi:10.1016/j.joca.2009.07.001).*
Jacobs HN, et al. (2016) Osteoarthritis and Cartilage—Abstracts. p. S435. Abstract No. 733.*
Tolg C, et al. (2012) Am J Pathol. 181(4):1250-1270.*
Esguerra KVN, et al. (2015) Integrative Biology. 7:1547-1560. (doi: 10.1039/c5ib00222b).*
International Search Report, dated Aug. 30, 2017 from corresponding PCT Application PCT/EP2017/064196.
Abuchowski et al. Effect of covalent attachment of polyethylene glycol on immunogenicity and circulating life of bovine liver catalase. J Biol Chem. Jun. 10, 1977;252(11):3582-6.
Kraus et al. The OARSI histopathology initiative—recommendations for histological assessments of osteoarthritis in the guinea pig. Osteoarthritis Cartilage. Oct. 2010;18 Suppl 3:S35-52.
Pastoureau et al. Cartilage, bone and synovial histomorphometry in animal models of osteoarthritis. Osteoarthritis Cartilage. Oct. 2010;18 Suppl 3:S106-12.
Silveri et al. Intra-articular injection of somatostatin in knee osteoarthritis: clinical results and IGF-1 serum levels. Int J Clin Pharmacol Res. 1994;14(2):79-85.
Silveri et al. Somatostatin a useful option for osteoarthritis of the knee. Inpharma Adis Press Australasia, Balgowlah, AU, Oct. 28, 1994.

* cited by examiner

*Primary Examiner* — Robert S Landsman
(74) *Attorney, Agent, or Firm* — Nixon & Vanderhye

(57) ABSTRACT

Disclosed are advances relates to peptides including a sequence SEQ ID NO: 1 for use in the treatment of osteoarthritis.

14 Claims, 3 Drawing Sheets
Specification includes a Sequence Listing.

METHODS FOR TREATING OSTEOARTHRITIS BY ADMINISTERING LINKED VARIANTS OF GROWTH HORMONE AND SOMATOSTATIN

FIELD OF INVENTION

The present invention relates to the treatment of osteoarthritis. In particular, the present invention relates to peptides for use in the treatment of osteoarthritis.

BACKGROUND OF INVENTION

Osteoarthritis is commonly related to a type of degenerative joint disease afflicting millions of individuals, and resulting in the breakdown of joint cartilage and of underlying bone, provoking in concerned subjects, joint pain, joint swelling, stiffness and decreased range of motion. Though it was previously thought to be a normal consequence of aging, it is now realized that osteoarthritis results from a complex interplay of multiple factors, including joint integrity, genetic predisposition, local inflammation, mechanical forces, and cellular and biochemical processes. In more than 10% of the cases, injuries can also cause post-traumatic osteoarthritis to develop and thus, affect individuals at any age.

Current treatments and researches are directed towards reduction of symptoms and prevention of disabilities, but no efficient and long-lasting pharmacologic therapies have been proven to prevent the progression of joint damage due to osteoarthritis. Among these treatments currently available, physical activity is considered an important part of the treatment plan. Studies show that simple activities and/or stretching exercises can reduce pain by maintaining a healthy weight and improving flexibility. Excess weight indeed adds additional stress to weight-bearing joints, such as the hips, knees, feet and back. Losing weight can help people with osteoarthritis reduce pain and limit further joint damage. Pain and anti-inflammatory medications, including analgesics, nonsteroidal anti-inflammatory drugs or corticosteroids, are also often considered in the treatment plan to alleviate osteoarthritis symptoms. These are available as creams, tablets or intra-articular injections. Finally, more severely suffering patients can consider the surgery option like arthroplasty, arthrodesis or osteotomy, to repair or replace damaged joints.

More recently, cell-based and biological therapies for osteoarthritis have been developed. For example, autologous chondrocyte implantation has been used for treatment of osteoarticular lesions for several decades. Chondrocyte-based therapy has shown its capacity to slow down the progression of osteoarthritis and delay joint replacement surgery, but numerous complications remain associated with like hypertrophy, disturbed fusion, delamination, and graft failure.

Finally, gene therapy has attracted the attention of scientists, to target the disease process rather than the symptoms. Both viral and non-viral vectors have been developed to carry the therapeutic genes to autologous chondrocytes, raising serious concerns about the immunogenicity of viral vectors; and the low and short-term efficiency of non-viral vectors. These gene therapies aim at inhibiting inflammatory and catabolic pathways, stimulating anabolic pathways to rebuild the matrix, impeding cell senescence, avoiding the pathological formation of osteophytes and/or preventing apoptosis. Numerous candidates for osteoarthritis gene therapy have been identified to date, like cytokines Interleukin-1 (IL-1), Tumor necrosis factor receptor (TNFR) and Interleukin-4 (IL-4) and their respective antagonists; matrix breakdown inhibitors Tissue inhibitor of metalloproteinases (TIMPs), Plasminogen activator inhibitors (PAIs) or serpins; apoptosis inhibitor B-cell lymphoma 2 (Bcl-2); cartilage growth factors; etc.

However, no effective, safe and easy-to-implement treatment is currently available. According to the World Health Organization, an estimated 10% to 15% of all adults have some degree of osteoarthritis. This prevalence is increasing due to population ageing and an increase in related factors such as obesity. According to the United Nations, by 2050, 130 million people worldwide will suffer from osteoarthritis, of whom 40 million will be severely disabled by the disease. These figures shed the light on the urgent need to develop a new treatment, easy to administrate and capable of curing instead of alleviating the symptoms.

Willing to develop peptides for treating osteoarthritis, the Applicant surprisingly showed that chimeric peptides comprising an amino acid sequence derived from growth hormone linked at its C-terminal extremity with an amino acid sequence derived from somatostatin may efficiently induce chondrocytes proliferation and differentiation, and may therefore be used for treating osteoarthritis.

The present invention thus relates to peptides for treating osteoarthritis.

SUMMARY

The invention thus relates to a peptide comprising an amino acids sequence SEQ ID NO: 1, or a fragment or variant thereof, wherein SEQ ID NO: 1 is the following:

(SEQ ID NO: 1)
$X_1$-Tyr-$X_2$-Leu-$X_3$-Ala-Gly-$X_4$-Lys-Asn-Phe-Phe-$X_5$ wherein:
$X_1$ is vacant or is valine or a sequence selected from:

$Z_1$-Val

Asp-$Z_1$-Val (SEQ ID NO: 5)
Ser-Asp-$Z_1$-Val (SEQ ID NO: 6)
$Z_2$-Ser-Asp-$Z_1$-Val
and (SEQ ID NO: 7)
Gly-$Z_2$-Ser-Asp-$Z_1$-Val wherein $Z_1$ is arginine and $Z_2$ threonine, or $Z_1$ is Ser-Asp or Ser-Asn and $Z_2$ is alanine;

$X_2$ is a sequence selected from Glu-Lys, Glu-Ser and Asp-Leu;

$X_3$ is vacant or is lysine or a sequence selected from:

Lys-Asp

Lys-Asp-Leu (SEQ ID NO: 8)
Lys-Asp-Leu-Glu (SEQ ID NO: 9)
Lys-Asp-Leu-Glu-Glu

```
                                         (SEQ ID NO: 10)
    Lys-Asp-Leu-Glu-Gly (SEQ ID NO: 11)
    Lys-Asp-Leu-Glu-Gly-Ile (SEQ ID NO: 12)
    Lys-Asp-Leu-Glu-Gly-Ile-Gln (SEQ ID NO: 13)
    Lys-Asp-Leu-Glu-Gly-Ile-Gln-Z₃
    and (SEQ ID NO: 14)
    Lys-Asp-Leu-Glu-Gly-Ile-Gln-Z₃-Leu
``` wherein $Z_3$ is alanine or threonine;

$X_4$ is an amino acid residue selected from cysteine, serine, tyrosine, phenylalanine, aspartic acid, glutamic acid, alanine and glycine; and $X_5$ is vacant or is a tryptophan residue or a sequence selected from:

```
    Trp-Lys

Trp-Lys-Thr (SEQ ID NO: 15)
    Trp-Lys-Thr-Phe (SEQ ID NO: 16)
    Trp-Lys-Thr-Phe-Thr (SEQ ID NO: 17)
    Trp-Lys-Thr-Phe-Thr-Ser (SEQ ID NO: 18)
    Trp-Lys-Thr-Phe-Thr-Ser-X₆
    and (SEQ ID NO: 19)
    Trp-Lys-Thr-Phe-Thr-Ser-X₆-Lys-Gln-Ala
``` wherein $X_6$ is an amino acid residue selected from cysteine, serine, tyrosine, phenylalanine, aspartic acid, glutamic acid, alanine and glycine;

for use in the treatment of osteoarthritis in a subject.

In one embodiment, the peptide consists in an amino acid sequence ranging from 11 to 50 amino acids residues, preferably ranging from 20 and 30 amino acid residues.

In one embodiment, $X_1$ is Gly-$Z_2$-Ser-Asp-$Z_1$-Val; and $X_5$ is Trp-Lys-Thr-Phe-Thr-Ser-$X_6$.

In one embodiment, the peptide comprises a sequence SEQ ID NO: 2, 3, 4 or 20:

```
                                         (SEQ ID NO: 2)
    Gly-Ala-Ser-Asp-Ser-Asp-Val-Tyr-Asp-Leu-Leu-Ala-

Gly-Ser-Lys-Asn-Phe-Phe-Trp-Lys-Thr-Phe-Thr-Ser-

Ser (SEQ ID NO: 3)
    Gly-Ala-Ser-Asp-Ser-Asp-Val-Tyr-Asp-Leu-Leu-Lys-

Ala-Gly-Ser-Lys-Asn-Phe-Phe-Trp-Lys-Thr-Phe-Thr-

Ser-Ser (SEQ ID NO: 4)
    Gly-Thr-Ser-Asp-Arg-Val-Tyr-Glu-Lys-Leu-Ala-Gly-

Ser-Lys-Asn-Phe-Phe-Trp-Lys-Thr-Phe-Thr-Ser-Ser (SEQ ID NO: 20)
    Gly-Ala-Ser-Asp-Ser-Asn-Val-Tyr-Asp-Leu-Leu-Lys-

Ala-Gly-Ser-Lys-Asn-Phe-Phe-Trp-Lys-Thr-Phe-Thr-

Ser-Ser.
```

In one embodiment, said peptide is to be administered by intra-articular injection in the joint to be treated.

In one embodiment, said peptide is to be administered at a final concentration in the joint ranging from $10^{-3}$ M to $10^{-7}$ M or from $10^{-4}$ M to $10^{-7}$ M.

The present invention further relates to a pharmaceutical composition containing at least one peptide for use as described in the present invention and one or more pharmaceutically acceptable excipient.

The present invention further relates to a medicament containing at least one peptide for use as described in the present invention.

The present invention further relates to a pharmaceutical unit dosage form containing at least one peptide for use as described in the present invention.

In one embodiment, the unit dosage form is a single use pre-filled, pre-dosed syringe, for local injection in the joint to be treated.

The present invention further relates to a pharmaceutical composition, a medicament, or a pharmaceutical unit dosage form as described hereinabove, wherein said pharmaceutical composition, medicament or pharmaceutical unit dosage for further contains at least one viscosupplementation agent.

In one embodiment, the at least one viscosupplementation agent is hyaluronic acid, preferably wherein hyaluronic acid is at a concentration ranging from 0.1% to 10%.

DEFINITIONS

In the present invention, the following terms have the following meanings:

The term "subject" refers to a mammal, preferably a human. In one embodiment of the invention, a subject may also refer to a horse, a cow or a pet, such as, for example, a dog, a cat, a guinea pig, a hamster, a rat, a mouse, a ferret, a rabbit and the like. In one embodiment, a subject may be a "patient".

The term "patient" refers to a subject, who/which is awaiting the receipt of, or is receiving medical care or was/is/will be the object of a medical procedure, or is monitored for the development of a disease.

The term "elderly" refers to a human subject or patient past 30 years-old (such as, for example, past about 40, 50, 60, 70, 80, 90 years-old or more), or to a non-human animal with equivalent age according to the specie.

The terms "treating", "treatment" or "alleviation" refer to both therapeutic treatment and prophylactic or preventative measures; wherein the object is to prevent or slow down (lessen) osteoarthritis. Those in need of treatment include those already with osteoarthritis as well as those prone to have osteoarthritis or those in whom osteoarthritis is to be prevented. A subject or mammal is successfully "treated" for osteoarthritis if, after receiving a therapeutic amount of a peptide according to the present invention, the patient shows observable and/or measurable reduction in or absence of one or more of the following: reduction or slow-down of the degradation of cartilage structure, maintenance or increase in cartilage thickness, relief to some extent of one or more of the symptoms associated with osteoarthritis; reduced morbidity, and/or improvement in quality of life issues. The above parameters for assessing successful treatment and improvement in osteoarthritis are readily measurable by routine procedures familiar to a physician.

The term "therapeutically effective amount" means level or amount of agent that is aimed at, without causing significant negative or adverse side effects to the target, (1) delaying or preventing the onset of osteoarthritis; (2) slowing down or stopping the progression, aggravation, or deterioration of one or more symptoms of osteoarthritis; (3) bringing about ameliorations of the symptoms of osteoarthritis; (4) reducing the severity or incidence of osteoarthritis; or (5) curing osteoarthritis. A therapeutically effective amount may be administered prior to the onset of osteoarthritis, for a prophylactic or preventive action. Alternatively or additionally, the therapeutically effective amount may be administered after initiation of osteoarthritis, for a therapeutic action.

The term "pharmaceutically acceptable excipient" refers to an excipient that does not produce an adverse, allergic or other untoward reaction when administered to an animal, preferably a human. It includes any and all solvents, dispersion media, coatings, antibacterial and antifungal agents, isotonic and absorption delaying agents and the like. For human administration, preparations should meet sterility, pyrogenicity, general safety and purity standards as required by regulatory offices, such as, for example, FDA Office or EMA.

The term "about" preceding a figure means plus or less 10% of the value of said figure.

DETAILED DESCRIPTION

The present invention relates to a peptide for use in the treatment of osteoarthritis. Indeed, the Applicant surprisingly demonstrated that the peptides of the invention are capable of inducing a local acceleration of chondrocytes proliferation and differentiation, and may therefore be used for treating osteoarthritis.

In one embodiment, the peptide of the invention is a synthetic peptide comprising a fragment of growth hormone (GH) sequence (such as, for example, human GH sequence in particular in an embodiment where the subject to be treated is a human) linked via an amino bond to a fragment of somatostatin sequence (such as, for example, human somatostatin sequence, in particular in an embodiment where the subject to be treated is a human).

In one embodiment, the peptide of the invention comprises or consists in SEQ ID NO: 1 or a fragment or variant thereof, wherein SEQ ID NO: 1 is the following:

(SEQ ID NO: 1)
X$_1$-Tyr-X$_2$-Leu-X$_3$-Ala-Gly-X$_4$-Lys-Asn-Phe-Phe-X$_5$ wherein:
X$_1$ is vacant or is valine or a sequence selected from:

Z$_1$-Val

Asp-Z$_1$-Val (SEQ ID NO: 5)
Ser-Asp-Z$_1$-Val (SEQ ID NO: 6)
Z$_2$-Ser-Asp-Z$_1$-Val and (SEQ ID NO: 7)
Gly-Z$_2$-Ser-Asp-Z$_1$-Val wherein Z$_1$ is arginine and Z$_2$ threonine, or Z$_1$ is Ser-Asp or Ser-Asn and Z$_2$ is alanine;
X$_2$ is a sequence selected from Glu-Lys, Glu-Ser and Asp-Leu;
X$_3$ is vacant or is lysine or a sequence selected from:

Lys-Asp

Lys-Asp-Leu (SEQ ID NO: 8)
Lys-Asp-Leu-Glu (SEQ ID NO: 9)
Lys-Asp-Leu-Glu-Glu (SEQ ID NO: 10)
Lys-Asp-Leu-Glu-Glu-Gly (SEQ ID NO: 11)
Lys-Asp-Leu-Glu-Glu-Gly-Ile (SEQ ID NO: 12)
Lys-Asp-Leu-Glu-Glu-Gly-Ile-Gln (SEQ ID NO: 13)
Lys-Asp-Leu-Glu-Glu-Gly-Ile-Gln-Z$_3$
and (SEQ ID NO: 14)
Lys-Asp-Leu-Glu-Glu-Gly-Ile-Gln-Z$_3$-Leu wherein Z$_3$ is alanine or threonine;
X$_4$ is an amino acid residue selected from cysteine, serine, tyrosine, phenylalanine, aspartic acid, glutamic acid, alanine and glycine; and
X$_5$ is vacant or is a tryptophan residue or a sequence selected from:

Trp-Lys

Trp-Lys-Thr (SEQ ID NO: 15)
Trp-Lys-Thr-Phe (SEQ ID NO: 16)
Trp-Lys-Thr-Phe-Thr (SEQ ID NO: 17)
Trp-Lys-Thr-Phe-Thr-Ser (SEQ ID NO: 18)
Trp-Lys-Thr-Phe-Thr-Ser-X$_6$
and (SEQ ID NO: 19)
Trp-Lys-Thr-Phe-Thr-Ser-X$_6$-Lys-Gln-Ala wherein X$_6$ is an amino acid residue selected from cysteine, serine, tyrosine, phenylalanine, aspartic acid, glutamic acid, alanine and glycine.

In one embodiment, X$_1$ is Gly-Z$_2$-Ser-Asp-Z$_1$-Val (SEQ ID NO: 7) wherein Z$_1$ and Z$_2$ are as described above; X$_2$, X$_3$ and X$_4$ are as described above; X$_5$ is Trp-Lys-Thr-Phe-Thr-Ser-X$_6$ (SEQ ID NO: 18), wherein X$_6$ is as described above.

In one embodiment, X$_1$ is Gly-Z$_2$-Ser-Asp-Z$_1$-Val (SEQ ID NO: 7) wherein Z$_1$ is Ser-Asp and Z$_2$ is alanine; X$_2$ is Asp-Leu; X$_3$ is vacant; X$_4$ is serine; X$_5$ is Trp-Lys-Thr-Phe- Thr-Ser-X$_6$ (SEQ ID NO: 18), wherein X$_6$ is serine. According to this embodiment, the peptide of the invention comprises or consists of SEQ ID NO: 2, a fragment or a variant thereof, wherein SEQ ID NO: 2 is the following:

```
                                    (SEQ ID NO: 2)
Gly-Ala-Ser-Asp-Ser-Asp-Val-Tyr-Asp-Leu-Leu-

Ala-Gly-Ser-Lys-Asn-Phe-Phe-Trp-Lys-Thr-Phe-

Thr-Ser-Ser
```

In another embodiment, X$_1$ is Gly-Z$_2$-Ser-Asp-Z$_1$-Val (SEQ ID NO: 7) wherein Z$_1$ is Ser-Asp and Z$_2$ is alanine; X$_2$ is Asp-Leu; X$_3$ is lysine; X$_4$ is serine; X$_5$ is Trp-Lys-Thr-Phe-Thr-Ser-X$_6$ (SEQ ID NO: 18), wherein X$_6$ is serine. According to this embodiment, the peptide of the invention comprises or consists of SEQ ID NO: 3, a fragment or a variant thereof, wherein SEQ ID NO: 3 is the following:

```
                                    (SEQ ID NO: 3)
Gly-Ala-Ser-Asp-Ser-Asp-Val-Tyr-Asp-Leu-Leu-Lys-

Ala-Gly-Ser-Lys-Asn-Phe-Phe-Trp-Lys-Thr-Phe-Thr-

Ser-Ser
```

In another embodiment, X$_1$ is Gly-Z$_2$-Ser-Asp-Z$_1$-Val (SEQ ID NO: 7) wherein Z$_1$ is arginine and Z$_2$ is threonine; X$_2$ is Glu-Lys; X$_3$ is vacant; X$_4$ is serine; X$_5$ is Trp-Lys-Thr-Phe-Thr-Ser-X$_6$ (SEQ ID NO: 18), wherein X$_6$ is serine. According to this embodiment, the peptide of the invention comprises or consists of SEQ ID NO: 4, a fragment or a variant thereof, wherein SEQ ID NO: 4 is the following:

```
                                    (SEQ ID NO: 4)
Gly-Thr-Ser-Asp-Arg-Val-Tyr-Glu-Lys-Leu-Ala-Gly-

Ser-Lys-Asn-Phe-Phe-Trp-Lys-Thr-Phe-Thr-Ser-Ser
```

In another embodiment, X$_1$ is Gly-Z$_2$-Ser-Asp-Z$_1$-Val (SEQ ID NO: 7) wherein Z$_1$ is Ser-Asn and Z$_2$ is alanine; X$_2$ is Asp-Leu; X$_3$ is lysine; X$_4$ is serine; X$_5$ is Trp-Lys-Thr-Phe-Thr-Ser-X$_6$ (SEQ ID NO: 18), wherein X$_6$ is serine. According to this embodiment, the peptide of the invention comprises or consists of SEQ ID NO: 20, a fragment or a variant thereof, wherein SEQ ID NO: 20 is the following:

```
                                   (SEQ ID NO: 20)
Gly-Ala-Ser-Asp-Ser-Asn-Val-Tyr-Asp-Leu-Leu-Lys-

Ala-Gly-Ser-Lys-Asn-Phe-Phe-Trp-Lys-Thr-Phe-Thr-

Ser-Ser
```

In one embodiment, the peptide of the invention consists in an amino acid sequence ranging from about 11 to about 50 amino acids residue, preferably ranging from 14 to about 40 amino acid residues, more preferably from about 20 to about 30 amino acid residues. In one embodiment, the peptide of the invention consists in 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids.

As used herein, "amino acids" are represented by their full name, their three letter code or their one letter code as well known in the art. Amino acid residues in peptides are abbreviated as follows: Phenylalanine is Phe or F; Leucine is Leu or L; Isoleucine is Ile or I; Methionine is Met or M; Valine is Val or V; Serine is Ser or S; Proline is Pro or P; Threonine is Thr or T; Alanine is Ala or A; Tyrosine is Tyr or Y; Histidine is His or H; Glutamine is Gln or Q; Asparagine is Asn or N; Lysine is Lys or K; Aspartic Acid is Asp or D; Glutamic Acid is Glu or E; Cysteine is Cys or C; Tryptophan is Trp or W; Arginine is Arg or R; and Glycine is Gly or G.

As used herein, the term "amino acids" includes both natural and synthetic amino acids, and both D and L amino acids. "Standard amino acid" or "naturally occurring amino acid" means any of the twenty standard L-amino acids commonly found in naturally occurring peptides. "Nonstandard amino acid residue" means any amino acid, other than the standard amino acids, regardless of whether it is prepared synthetically or derived from a natural source. For example, naphtlylalanine can be substituted for tryptophan to facilitate synthesis. Other synthetic amino acids that can be substituted include, but are not limited to, L-hydroxypropyl, L-3,4-dihydroxyphenylalanyl, alpha-amino acids such as L-alpha-hydroxylysyl and D-alpha-methylalanyl, L-alpha-methylalanyl, beta-amino acids, and isoquinolyl. Also, threonine, alanine, tryptophan and phenylalanine residues can belong to the D-form, for the peptide to be more resistant to peptidases.

As used herein, "amino acid" also encompasses chemically modified amino acids, including but not limited to salts, amino acid derivatives (such as amides), and substitutions. Amino acids contained within the peptides of the present invention, and particularly at the carboxy- or amino-terminus, can be modified by methylation, amidation, acetylation or substitution with other chemical groups which can change the peptide's circulating half-life without adversely affecting their activity. Additionally, a disulfide linkage may be present or absent in the peptides of the invention.

The peptides useful in the present invention may comprise naturally standard amino acids or non-standard amino acids. Peptide mimetics include peptides having the following modifications: i) peptides wherein one or more of the peptidyl —C(O)NR— linkages (bonds) have been replaced by a non-peptidyl linkage such as a —CH$_2$-carbamate linkage (—CH$_2$OC(O)NR—), a phosphonate linkage, a —CH$_2$-sulfonamide (—CH$_2$—S(O)$_2$NR—) linkage, a urea (—NHC(O)NH—) linkage, a —CH$_2$-secondary amine linkage, or with an alkylated peptidyl linkage (—C(O)NR—) wherein R is C$_1$-C$_4$ alkyl; ii) peptides wherein the N-terminus is derivatized to a —NRR$^1$ group, to a —NRC(O)R group, to a —NRC(O)OR group, to a —NRS(O)$_2$R group, to a —NHC(O)NHR group where R and R$^1$ are hydrogen or C$_1$-C$_4$ alkyl with the proviso that R and R$^1$ are not both hydrogen; iii) peptides wherein the C terminus is derivatized to —C(O)R$^2$ where R$^2$ is selected from the group consisting of C$_1$-C$_4$ alkoxy, and —NR$^3$R$^4$ where R$^3$ and R$^4$ are independently selected from the group consisting of hydrogen and C$_1$-C$_4$ alkyl.

In one embodiment, the N- and C-termini of the peptides useful in the present invention may be optionally protected against proteolysis. For instance, the N-terminus may be in the form of an acetyl group, and/or the C-terminus may be in the form of an amide group.

Therefore, in one embodiment, the peptide of the invention comprises or consists in the following amino acid sequence:
Ac-Gly-Ala-Ser-Asp-Ser-Asp-Val-Tyr-Asp-Leu-Leu-Ala-Gly-Ser-Lys-Asn-Phe-Phe-Trp-Lys-Thr-Phe-Thr-Ser-Ser-NH$_2$ (SEQ ID NO: 2 protected with an acetyl group in N-term and with an amide group in C-term); or Ac-Gly-Ala-Ser-Asp-Ser-Asp-Val-Tyr-Asp-Leu-Leu-Lys-Ala-Gly-Ser-Lys-Asn-Phe-Phe-Trp-Lys-Thr-Phe-Thr-Ser-Ser-NH$_2$ (SEQ ID NO: 3 protected with an acetyl group in N-term and with an amide group in C-term); or Ac-Gly-Thr-Ser-Asp-Arg-Val-Tyr-Glu-Lys-Leu-Ala-Gly-Ser-Lys-Asn-Phe-Phe-Trp-Lys-Thr-Phe-Thr-Ser-Ser-NH$_2$ (SEQ ID NO: 4 protected with an acetyl group in N-term and with an amide group in C-term); or Ac-Gly-Ala-Ser-Asp-Ser-Asn-Val-Tyr-Asp-Leu-Leu-Lys-Ala-Gly-Ser-Lys-Asn-Phe-Phe-Trp-Lys-Thr-Phe-Thr-Ser-Ser-NH$_2$ (SEQ ID NO: 20 protected with an acetyl group in N-term and with an amide group in C-term).

Internal modifications of the peptides to be resistant to proteolysis are also envisioned, e.g. wherein at least a —CONH— peptide bond is modified and replaced by a (CH$_2$NH) reduced bond, a (NHCO) retro-inverso bond, a (CH$_2$—O) methylene-oxy bond, a (CH$_2$—S) thiomethylene bond, a (CH$_2$CH$_2$) carba bond, a (CO—CH$_2$) cetomethylene bond, a (CHOH—CH$_2$) hydroxyethylene bond), a (N—N) bound, a E-alcene bond or also a —CH═CH-bond.

In one embodiment of the invention, the polypeptides as described here above are modified by means well-known in the art, for instance by the addition of one or more functional group such as a phosphate, acetate, lipid or carbohydrate group, and/or by the addition of one or more protecting group.

For example, the polypeptides can be modified by the addition of one or more functional groups such as phosphate, acetate, or various lipids and carbohydrates. The polypeptides of the invention can also exist as polypeptide derivatives. The term "polypeptide derivative" refers to compound having an amino group (—NH—), and more particularly, a peptide bond. Polypeptides may be regarded as substituted amides. Like the amide group, the peptide bond shows a high degree of resonance stabilization. The C—N single bond in the peptide linkage has typically about 40 percent double-bond character and the C═O double bond about 40 percent single-bond character. "Protecting groups" are those groups that prevent undesirable reactions (such as proteolysis) involving unprotected functional groups. Specific examples of amino protecting groups include formyl; trifluoroacetyl; benzyloxycarbonyl; substituted benzyloxycarbonyl such as (ortho- or para-) chlorobenzyloxycarbonyl and (ortho- or para-) bromobenzyloxycarbonyl; and aliphatic oxycarbonyl such as t-butoxycarbonyl and t-amiloxycarbonyl. The carboxyl groups of amino acids can be protected through conversion into ester groups. The ester groups include benzyl esters, substituted benzyl esters such as methoxybenzyl ester; alkyl esters such as cyclohexyl ester, cycloheptyl ester or t-butyl ester. The guanidino moiety may be protected by nitro; or arylsulfonyl such as tosyl, methoxybenzensulfonyl or mesitylenesulfonyl, even though it does not need a protecting group. The protecting groups of imidazole include tosy, benzyl and dinitrophenyl. The indole group of tryptophan may be protected by formyl or may not be protected.

Peptides useful in the present invention can also be covalently bound to a polyethylene glycol (PEG) molecule by their C-terminal terminus or a lysine residue, notably a PEG of 1500 MW or 4000 MW, for a decrease in urinary clearance and in therapeutic doses used and for an increase of water solubility, mobility in solution and half-life in blood plasma, all with a low immunogenicity. The binding of PEG is as described by Abuchowski et al., (J. Biol. Chenu., 1977, 252: 3582-3586). In a further aspect of the invention, two or more PEG molecules are bound in each anchorage site. In yet another embodiment, peptide half-life is increased by including the peptide in a biodegradable and biocompatible polymer material for drug delivery system forming microspheres. Polymers and copolymers are, for instance, poly (D,L-lactide-co-glycolide) (PLGA) (as illustrated in US2007/0184015, SoonKap Hahn et al.).

Other examples of modifications used to prevent degradation of the polypeptides by endopeptidases or exopeptidases include N-terminal modifications such as acetylation or glycosylation, C-terminal modifications such as amidation and use of unnatural amino acids β-amino and α-trifluoromethyl amino acids) at particular sites within the polypeptides.

Another alternative to increase polypeptide molecular size is the genetic fusion of the polypeptides to the Fc domain of human gamma immunoglobulin or the fusion of the polypeptides to albumin.

In one embodiment, the peptide of the invention is a variant of SEQ ID NO: 1, preferably a variant of SEQ ID NO: 2, 3, 4 or 20.

A peptide "variant" as the term is used herein, is a peptide that typically differs from a peptide specifically disclosed herein in one or more substitutions, deletions, additions and/or insertions. Such variants may be naturally occurring or may be synthetically generated, for example, by modifying one or more of the above peptide sequences and evaluating one or more biological activities of the peptide as described herein and/or using any of a number of techniques well known in the art. Modifications may be made in the structure of peptides and still obtain a functional molecule that encodes a variant or derivative peptide with desirable characteristics.

When it is desired to alter the amino acid sequence of a peptide to create an equivalent, or even an improved, variant or portion of a ligand of the invention, one skilled in the art will typically change one or more of the codons of the encoding DNA sequence. For example, certain amino acids may be substituted by other amino acids in a protein structure without appreciable loss of its ability to bind cell surface receptor, preferably cell surface nutrient transporters. Since it is the binding capacity and nature of a protein that defines that protein's biological functional activity, certain amino acid sequence substitutions can be made in a protein sequence, and, of course, its underlying DNA coding sequence, and nevertheless obtain a protein with similar properties. It is thus contemplated that various changes may be made in the peptide sequences, or corresponding DNA sequences that encode said peptides without appreciable loss of their biological utility or activity. In many instances, a peptide variant will contain one or more conservative substitutions. A "conservative substitution" is one in which an amino acid is substituted by another amino acid that has similar properties, such that one skilled in the art of peptide chemistry would expect the secondary structure and hydropathic nature of the peptide to be substantially unchanged. As outlined above, amino acid substitutions are generally therefore based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine. Amino acid substitutions may further be made on the basis of similarity in polarity, charge, solubility, hydrophobicity, hydrophilicity and/or the amphipathic nature of the residues. For example, negatively charged amino acids include aspartic acid and glutamic acid; positively charged amino acids include histidine, lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his.

As used herein, the term "conservative amino acid substitution" may further be defined as an amino acid exchange within one of the following five groups:

I. Small aliphatic, nonpolar or slightly polar residues: Ala, Ser, Thr, Pro, Gly;
II. Polar, negatively charged residues and their amides: Asp, Asn, Glu, Gln;
III. Polar, positively charged residues: His, Arg, Lys;
IV. Large, aliphatic, nonpolar residues: Met, Leu, Ile, Val, Cys;
V. Large, aromatic residues: Phe, Tyr, Trp.

A variant may also, or alternatively, contain non-conservative changes. In a preferred embodiment, variant peptides differ from a native sequence by substitution, deletion or addition of 1, 2, 3, 4, 5, 6, 7, 8, 9 or 10 amino acids. Variants may also (or alternatively) be modified by, for example, the deletion or addition of amino acids that have minimal influence on the immunogenicity, secondary structure and hydropathic nature of the peptide. Therefore, in one embodiment, a variant of SEQ ID NO: 1, 2, 3, 4 or 20 is a peptide wherein 1, 2, 3, 4, 5, 6, 7, 8, 9 or 10 amino acids from the sequence of SEQ ID NO: 1, 2, 3, 4 or 20 respectively is/are absent, or substituted by any amino acid, or wherein 1, 2, 3, 4, 5, 6, 7, 8, 9 or 10 amino acids (either contiguous or not) is/are added.

In one embodiment, a variant of SEQ ID NO: 1, 2, 3, 4 or 20 is a peptide having the sequence of SEQ ID NO: 1, 2, 3, 4 or 20 and 1, 2, 3, 4, 5, 6, 7, 8, 9 or 10 additional amino acids in C-term and/or in N-term.

In one embodiment, a variant of SEQ ID NO: 1, 2, 3 4 or 20 is a peptide showing at least about 70% identity with SEQ ID NO: 1, 2, 3, 4 or 20 respectively, preferably at least about 80, 85, 90, 91, 92, 93, 94, 95, 96, 97, 98, 99% identity or more.

The term "identity", when used in a relationship between the sequences of two or more polypeptides, refers to the degree of sequence relatedness between polypeptides, as determined by the number of matches between strings of two or more amino acid residues. "Identity" measures the percent of identical matches between the smaller of two or more sequences with gap alignments (if any) addressed by a particular mathematical model or computer program (i.e., "algorithms"). Identity of related polypeptides can be readily calculated by known methods. Such methods include, but are not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; Sequence Analysis Primer, Gribskov, M. and Devereux, J., eds., M. Stockton Press, New York, 1991; and Carillo et al., SIAM J. Applied Math. 48, 1073 (1988). Preferred methods for determining identity are designed to give the largest match between the sequences tested. Methods of determining identity are described in publicly available computer programs. Preferred computer program methods for determining identity between two sequences include the GCG program package, including GAP (Devereux et al., Nucl. Acid. Res. 2, 387 (1984); Genetics Computer Group, University of Wisconsin, Madison, Wis.), BLASTP, BLASTN, and FASTA (Altschul et al., J. Mol. Biol. 215, 403-410 (1990)). The BLASTX program is publicly available from the National Center for Biotechnology Information (NCBI) and other sources (BLAST Manual, Altschul et al. NCB/NLM/NIH Bethesda, Md. 20894; Altschul et al., supra). The well-known Smith Waterman algorithm may also be used to determine identity.

In one embodiment, tryptophan residue of the peptides can be linked to a $C_1$-$C_3$ alkyl group (methyl, ethyl, propyl, isopropyl) for the peptides to resist to oxidation. A tryptophan residue may for example be present when $X_5$ is in sequence set forth as SEQ ID NO: 1, thus being in position 19 in sequence set forth as SEQ ID NO: 2; in position 20 in sequence set forth as SEQ ID NO: 3 or SEQ ID NO: 20; in position 18 in sequence set forth as SEQ ID NO: 4.

The peptides described herein can be produced synthetically by chemical synthesis or enzymatic synthesis as it is well known in the art. Alternatively, nucleotide sequences encoding the peptides of the invention can be introduced into a protein expression vector and produced in a suitable host organism (e.g., bacteria, insect cells, etc), then purified. In a preferred embodiment, peptides are obtained by stepwise condensation of amino acids residue, either by condensation of a preformed fragment already containing an amino acid sequence in appropriate order, or by condensation of several fragments previously prepared, while protecting the amino acid functional groups except those involved in peptide bond during condensation. In particular, the peptides can be synthesized according to the method originally described by Merrifield.

An additional polypeptide ("tag") can be added on for the purpose of purifying or identifying or purifying the peptides. Protein tags make it possible, for example, for the peptides to be adsorbed, with high affinity, to a matrix, and for the matrix then to be washed stringently with suitable buffers without the complex being eluted to any significant extent, and for the adsorbed complex subsequently to be eluted selectively. Examples of protein tags which are known to the skilled person are a $(His)_6$ tag, a Myc tag, a FLAG tag, a hemagglutinin tag, a glutathione transferase (GST) tag, intein having an affinity chitin-binding tag or maltose-binding protein (MBP) tag. These protein tags can be located N-terminally, C-terminally and/or internally.

Advantageously, even when administered in an iterate way, peptides described herein do not induce anti-peptide or anti-GH antibody production, in contrast with immunogenic peptides of the art, which cause antibody production leading to endogenous GH neutralization and thus, to biological activity neutralization.

The present invention also relates to a composition comprising or consisting or consisting essentially of at least one peptide comprising SEQ ID NO: 1 (in particular a peptide having a sequence SEQ ID NO: 2-4 or 20) as described hereinabove or a fragment or variant thereof.

The invention also relates to a pharmaceutical composition comprising or consisting or consisting essentially of at least one peptide comprising SEQ ID NO: 1 in particular a peptide having a sequence SEQ ID NO: 2-4 or 20) as described hereinabove or a fragment or variant thereof and at least one pharmaceutically acceptable excipient.

The invention also relates to a medicament comprising or consisting or consisting essentially of at least one peptide comprising SEQ ID NO: 1 as described hereinabove or a fragment or variant thereof.

In one embodiment, the composition, pharmaceutical composition or medicament of the invention is for use for treating osteoarthritis in a subject in need thereof.

As used herein, the term "consisting essentially of", with reference to a composition, pharmaceutical composition or medicament of the invention, means that the at least one peptide of the invention is the only one therapeutic agent or agent with a biologic activity within said composition, pharmaceutical composition or medicament.

Examples of suitable excipients include, but are not limited to, water, saline, Ringer's solution, dextrose solution, and solutions of ethanol, glucose, sucrose, dextran, mannose, mannitol, sorbitol, polyethylene glycol (PEG), phosphate, acetate, gelatin, collagen, Carbopol®, vegetable oils, and the like. One may additionally include suitable preservatives, stabilizers, antioxidants, antimicrobials, and buffering agents, such as, for example, BHA, BHT, citric acid, ascorbic acid, tetracycline, and the like.

Other examples of pharmaceutically acceptable excipients that may be used in the composition of the invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

In one embodiment, the composition, pharmaceutical composition or medicament of the invention may comprise some excipients, such as, for example, surfactants (e.g. hydroxypropylcellulose); suitable carriers, such as, for example, solvents and dispersion media containing, for example, water, ethanol, polyol (e.g. glycerol, propylene glycol, and liquid polyethylene glycol, and the like), suitable mixtures thereof, and vegetable oils, such as, for example, peanut oil and sesame oil; isotonic agents, such as, for example, sugars or sodium chloride; coating agents, such as, for example, lecithin; agents delaying absorption, such as, for example, aluminum monostearate and gelatin; preservatives, such as, for example, benzalkonium chloride, benzethonium chloride, chlorobutanol, thimerosal and the like; buffers, such as, for example, boric acid, sodium and potassium bicarbonate, sodium and potassium borates, sodium and potassium carbonate, sodium acetate, sodium biphosphate and the like; tonicity agents, such as, for example, dextran 40, dextran 70, dextrose, glycerin, potassium chloride, propylene glycol, sodium chloride; antioxidants and stabilizers, such as, for example, sodium bisulfite, sodium metabisulfite, sodium thiosulfite, thiourea and the like; non-ionic wetting or clarifying agents, such as, for example, polysorbate 80, polysorbate 20, poloxamer 282 and tyloxapol; viscosity modifying agents, such as, for example dextran 40, dextran 70, gelatin, glycerin, hydroxyethylcellulose, hydroxmethylpropylcellulose, lanolin, methylcellulose, petrolatum, polyethylene glycol, polyvinyl alcohol, polyvinylpyrrolidone, carboxymethylcellulose; and the like.

In one embodiment, the composition, pharmaceutical composition or medicament may comprise a pharmaceutically acceptable salt of the peptide of the invention.

Examples of the pharmaceutically acceptable salt include salts with inorganic bases, salts with organic bases, salts with inorganic acids, salts with organic acids, salts with basic or acidic amino acids and the like. Examples of salts with an inorganic base include, but are not limited to, alkali metal salts, such as a sodium salt and a potassium salt; an alkaline earth metal salt such as a calcium salt and a magnesium salt; an aluminum salt; and an ammonium salt. Examples of salts with an organic base include, but are not limited to, salts with trimethylamine, triethylamine, pyridine, picoline, 2,6-lutidine, ethanolamine, diethanolamine, triethanolamine, cyclohexylamine, dicyclohexylamine and N,N'-dibenzylethylenediamine. Examples of salts with an inorganic acid include, but are not limited to, salts with hydrochloric acid, boric acid, nitric acid, sulfuric acid and phosphoric acid. Examples of salts with an organic acid include, but are not limited to, salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid and p-toluenesulfonic acid. Examples of salts with a basic amino acid include, but are not limited to, salts with arginine, lysine and ornithine. Examples of salts with an acidic amino acid include, but are not limited to, salts with aspartic acid and glutamic acid. The list of suitable salts is disclosed in Remington's Pharmaceutical Sciences, 17th ed., Mack Publishing Company, Easton, Pa., p 1418, 1985, the entire disclosure of which is incorporated herein by reference.

In one embodiment, the amount of peptide of the invention within the composition, pharmaceutical composition or medicament of the invention is a therapeutically effective amount and ranges from about 0.01 to 90% in volume, preferably from 0.1% to 10% in volume, more preferably from 1% to 5% in volume to the total volume of the composition, pharmaceutical composition or medicament of the invention. In another embodiment, the therapeutically effective amount ranges from about $10^{-9}$ M to about $10^{-1}$ M, preferably from about $10^{-8}$ M to about $10^{-2}$ M, and more preferably from about $10^{-7}$ M to about $10^{-3}$ M. These amounts are routinely adaptable by the skilled artisan, who is able to choose the best quantity to administer to a patient to achieve recovery.

According to one embodiment, peptides described herein are to be administrated together with at least one viscosupplementation agent. Therefore, in one embodiment, the composition, pharmaceutical composition or medicament of the invention further comprises at least one viscosupplementation agent.

Examples of viscosupplementation agents include, but are not limited to, a glycosaminoglycan, most commonly a non-sulfated glycosaminoglycan including hyaluronic acid, hylan, hyaluronan and related.

In a preferred embodiment, the at least one viscosupplementation agent is hyaluronic acid, preferably non-reticulated hyaluronic acid. In one embodiment, the viscosupplementation agent is hyaluronic acid with a molecular weight ranging from about 100 to about 5000 kDa, preferably from about 400 to about 1000 kDa, preferably non-reticulated hyaluronic acid with a molecular weight ranging from about 100 to about 5000 kDa, preferably from about 400 to about 1000 kDa. In one embodiment, the viscosupplementation agent is hyaluronic acid with a molecular weight ranging from about 600 to about 1000 kDa, preferably non-reticulated hyaluronic acid with a molecular weight ranging from about 600 to about 1000 kDa.

In another embodiment, the viscosupplementation agent, preferably hyaluronic acid, is present in the composition, pharmaceutical composition or medicament of the invention at a concentration ranging from about 0.1% to about 10%, preferably about 0.25% to about 5%, preferably about 0.25% to about 2%, preferably about 1% (percentages are in weight to the total volume of the composition, i.e. 1% corresponds to a concentration of 10 mg/ml).

Indeed, the applicant shows that hyaluronic acid induces a significant stabilization of the chimeric peptide in water solution (see Examples). Raman spectroscopy experiments have indeed shown an unstable structure in water of peptides with sequence set forth as SEQ ID NO: 1, reflected by the presence of four different conformations among which, three are quantitatively equivalent; whereas peptide with sequence set forth as SEQ ID NO: 1 in presence of hyaluronic acid have a stabilized β-hairpin conformation. Without willing to be bound to a theory, the Applicant suggests that this conformation allows somatostatin residues to be exposed for their specific and high-affinity binding to their receptors.

The present invention further relates to the use of peptides described herein, optionally combined with a viscosupplementation agent, for the treatment of osteoarthritis in a subject in need thereof. Indeed, the Applicant demonstrated that the peptides described herein act directly on chondrocytes, allowing them to differentiate, multiply, spread and produce a better quality cartilaginous matrix. These peptides show a long-term efficiency (up to 5 months after injection) on the thickness of the joint as well as the quality of the cartilaginous matrix (see Examples).

In one embodiment, the subject is affected, preferably is diagnosed, with osteoarthritis. In a first aspect, the subject is an elderly individual (such as, for example, an individual of more than 30, 40, 50, 60, 70, 80, 90 or more year-old) suffering from osteoarthritis. In a second aspect, the subject is an injured individual suffering from post-traumatic osteoarthritis.

In one embodiment, the subject is affected by grade 0, 1, 2, 3, or 4 osteoarthritis, according to the Kellgren-Lawrence grade (or K-L system). According to this scoring tool, grade 0 corresponds to the absence of radiographic features of osteoarthritis; grade 1 corresponds to possible joint space narrowing and osteophyte formation; grade 2 corresponds to definite osteophyte formation with possible joint space narrowing; grade 3 corresponds to multiple osteophytes, definite joint space narrowing, sclerosis and possible bony deformity; and grade 4 corresponds to large osteophytes, marked joint space narrowing, severe sclerosis and definite bony deformity.

In one embodiment, the subject is affected by grade 0, 1 or 2 osteoarthritis. In another embodiment, the subject is affected by grade 0 or 1 osteoarthritis.

In one embodiment, the peptide, composition, pharmaceutical composition or medicament of the invention is for preventing osteoarthritis, preferably in a subject at risk of developing osteoarthritis.

In another embodiment, the subject is at risk of developing osteoarthritis. Examples of risk factors include, but are not limited to, genetic factors, familial history of osteoarthritis, misalignments of bones caused by congenital or pathogenic causes, trauma, mechanical injury, excess body weight and obesity, loss of strength in the muscles supporting a joint, impairment of peripheral nerves leading to sudden or uncoordinated movements, alkaptonuria, congenital disorders of joints, diabetes, Ehlers-Danlos Syndrome, hemochromatosis and Wilson's disease, injury to joints or ligaments, ligamentous deterioration or instability, Marfan syndrome, joint infection and the like.

In one embodiment, the peptide, composition, pharmaceutical composition or medicament of the invention is for curing osteoarthritis in a subject already affected with osteoarthritis.

In one embodiment, the peptide, composition, pharmaceutical composition or medicament of the invention is for preventing aggravation of osteoarthritis in a subject already affected with osteoarthritis, such as, for example, in a subject with grade 0, 1 or 2 osteoarthritis according to the K-L system.

In one embodiment, the at least one peptide of the invention is, or is to be administrated by intra-articular injection in the joint to be treated.

In one embodiment, the targeted concentration of the peptide of the invention within the joint after administration ranges from about $10^{-9}$ M to about $10^{-2}$ M, preferably from about $10^{-8}$ M to about $10^{-3}$ M, and more preferably from about $10^{-7}$ M to about $10^{-3}$ M.

In one embodiment, the targeted concentration of the peptide of the invention within the joint after administration ranges from about $10^{-7}$ M to about $10^{-4}$ M. The concentration of therapeutically effective amount of peptide to be administrated to reach such intra-articular concentration depends on the size of the joint and the volume of synovial fluid inside it. These factors vary according to the nature of the joint, the age and the species of the subject to be treated. Theses parameters are well-known from those skilled in the art, in particular medical practitioners and veterinarians. For example, the volume of synovial fluid within a knee is usually of about 6-7 mL in human, about 500 µl for rabbit, and about 240 µl for dog.

Therefore, in one embodiment, for treating osteoarthritis in a human knee, 2 mL of a composition comprising a peptide of the invention (preferably a peptide as set forth as SEQ ID NO: 2 or SEQ ID NO: 3 or SEQ ID NO: 20), and optionally hyaluronic acid, can be injected in the joint. In veterinarian cases, this volume can be adjusted depending on the species.

In one embodiment, the composition, pharmaceutical composition or medicament is administered once, twice, three times or more, such as, for example, 4, 5, 6, 7, 8, 9, or 10 times, or until complete treatment of osteoarthritis.

In one embodiment, when the composition, pharmaceutical composition or medicament is administered several times, the interval between two administrations is of about 1, 2, 3, 4, 5, 6, 7 days, or of about 1, 2, 3, 4 weeks or of about 1, 2, 3, 4, 5, 6, 7, 8, 9, 10, 11, or 12 months or more.

In one embodiment, the composition, pharmaceutical composition or medicament of the invention is administered three times with a one-week-interval.

In one embodiment, before use, the peptide of the invention is sterilized, preferably by filtration or autoclaving. In another embodiment, before use, the composition of the invention comprising a peptide and a viscosupplementation agent is sterilized, preferably by filtration or autoclaving. In another embodiment, the peptide and the viscosupplementation agents are separately sterilized before mixing and use.

In one embodiment, peptides described herein are contained in a pharmaceutical unit dosage form. Preferably, this dosage unit is a single use pre-filled, pre-dosed syringe, for local injection in the joint to be treated. The present invention thus further relates to a unit dosage form (such as, for example, a pre-filled syringe) comprising a peptide of the invention, and optionally a viscosupplementation agent, such as, for example, hyaluronic acid. In one embodiment, the pharmaceutical unit dosage form is sterilized, preferably by filtration.

The concentration of peptide in the pharmaceutical unit dosage form depends on the size of the joint and the volume of synovial fluid inside it. These factors vary according to the nature of the joint, the age and the species of the subject to be treated.

In one embodiment, the pharmaceutical unit dosage form contains 2 mL of a composition, pharmaceutical composition or medicament comprising a peptide of the invention at a concentration suitable for administration of the peptide with a final concentration in the joint ranging from about $10^{-7}$ M to about $10^{-3}$ M or from about $10^{-7}$M to about $10^{-4}$ M, and optionally a viscosupplementation agent, preferably hyaluronic acid.

The present invention further relates to a kit of part comprising a first pharmaceutical unit dosage form comprising a peptide of the invention, and a second pharmaceutical unit dosage form comprising a viscosupplementation agent.

In one embodiment, both dosage units of the kit of part are a single use pre-filled, pre-dosed syringe.

In another embodiment, in the kit of part, the pharmaceutical unit dosage form comprising the viscosupplementaion agent is a single use pre-filled, pre-dosed syringe, wherein the viscosupplementation agent is preferably sterilized by autoclaving, and the pharmaceutical unit dosage form comprising the peptide of the invention is a vial, wherein preferably the peptide is sterilized by filtration.

The present invention further relates to a method for treating osteoarthritis in a subject in need thereof, wherein said method comprises administering a peptide of the present invention to the subject, and optionally a viscosupplementation agent (preferably hyaluronic acid). Preferably, a therapeutically effective amount of the peptide of the invention is administered to the subject.

Indeed, peptides described herein act directly on chondrocytes in the joint. As shown in the Examples, in vivo data obtained from Guinea Pig show a long term (5 months) efficiency on the thickness of the joint as well as the quality of the cartilaginous matrix. Moreover, in vivo data obtained from rabbit show a short term efficiency for reducing osteoarthritis lesions severity and size.

The present invention thus further relates to a method to differentiate chondrocytes and/or to multiply chondrocytes and/or to spread chondrocytes and/or to produce cartilaginous matrix, wherein said method comprises administering a peptide of the invention, and optionally a viscosupplementation agent (preferably hyaluronic acid).

The present invention further relates to a method for slowing-down or preventing cartilage degradation in a subject, wherein said method comprises administering a peptide of the present invention to the subject, and optionally a viscosupplementation agent (preferably hyaluronic acid). In one embodiment, said subject is affected with osteoarthritis, preferably with grade 0, 1 or 2 osteoarthritis.

The present invention further relates to a method for maintaining or increasing cartilage thickness in a subject, wherein said method comprises administering a peptide of the present invention to the subject, and optionally a viscosupplementation agent (preferably hyaluronic acid). In one embodiment, said subject is affected with osteoarthritis, preferably with grade 0, 1 or 2 osteoarthritis.

The present invention further relates to a method for decreasing the severity or size of osteoarthritis lesions, or for preventing an increase in severity or size of osteoarthritis lesions in a subject, wherein said method comprises administering a peptide of the present invention to the subject, and optionally a viscosupplementation agent (preferably hyaluronic acid).

EXAMPLES

Figure 1:
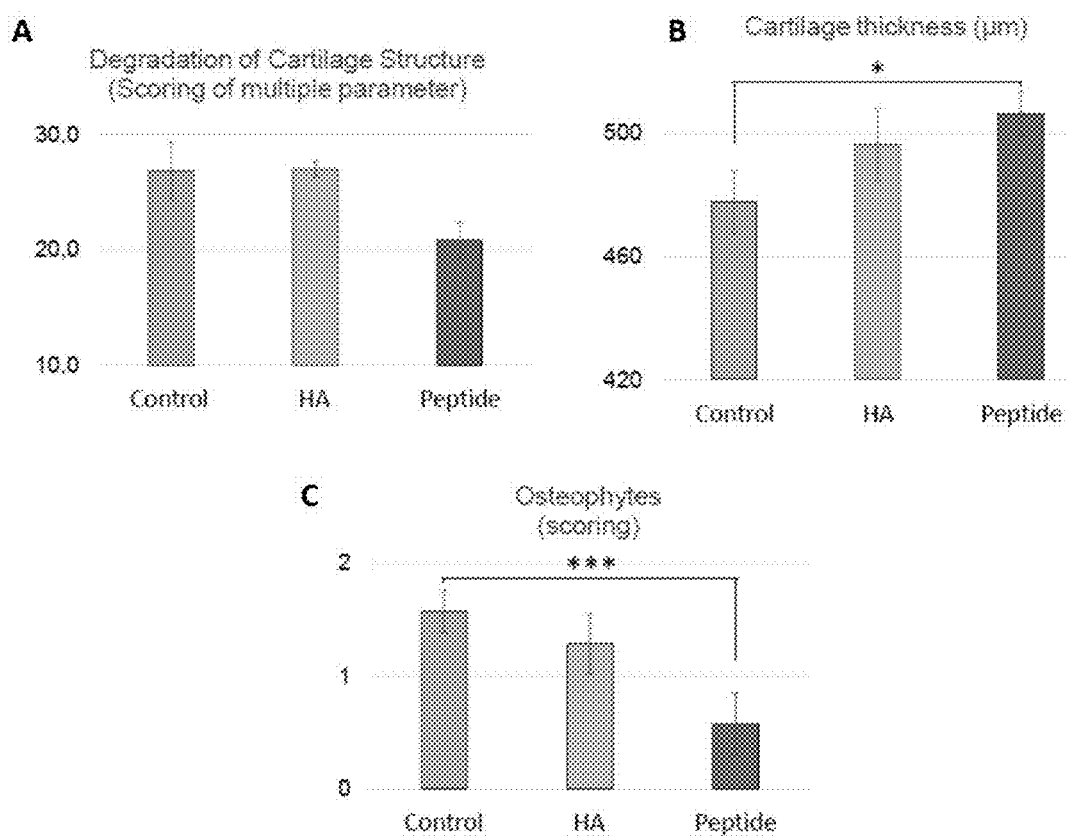
FIG. 1 is a combination of graphs showing in vivo efficiency tests carried out in Guinea Pig for hyaluronic acid versus peptide with sequence set forth as SEQ ID NO: 4 ("peptide"). (A) the histogram illustrates the sum of the scores representing the degradation of several structures in the joint, in particular the presence of osteophytes, the degradation of matrix proteoglycans, the degradation of the synovial membrane, the presence of abnormal cells, etc. It shows a significantly decreased degradation of cartilage structure in presence of peptide with sequence set forth as SEQ ID NO: 4 as compared to both control and hyaluronic acid alone. (B) the histogram shows an increased cartilage thickness in presence of both hyaluronic acid or peptide with sequence set forth as SEQ ID NO: 4. * $p<0.05$. (C) the histogram shows a decreased osteophytes scoring. ** $p<0.001$.

The present invention is further illustrated by the following examples.

Example 1: In Vivo Effect of the Peptide of the Invention

Sample Preparation

Peptide of the invention (corresponding to SEQ ID NO: 4) was dissolved at 2.5 mg/ml in water for injection (CDM Lavoisier) to make a stock solution conserved at −20° C. The syringe was prepared by aspiration of 50 µl of peptide work solution prepared just before use at $10^{-7}$ M (other concentrations are tested) in NaCl 0.9% and kept on ice until use.

Animal IA Injection

The study was performed on male Duncan-Hartley guinea pigs (Harlan), whose particularity is to be affected with age of spontaneous and progressive degeneration of the knee that closely resembles knee osteoarthritis (OA) in humans. Seven 5-month-old animals (weighing 879 g.+/−58.1) were injected per group. Animals were treated in accordance with institutional animal care guidelines. Animals were anesthetized with an anesthesia module (Minerva) with a rapid induction device (4% isoflurane) and anesthesia was maintained using a specific device mask in guinea coaxial (2.5% isoflurane). 50 µl of the peptide of the invention or control—salt solution or Hyalgan® (10 mg/ml solution of MW 500-730 kDa hyaluronic—Laboratoire Expanscience, available in the market)—were injected on each hind legs of the animal into the joint space from the lateral side using a 29 G needle. This was followed by passive knee joint movements to facilitate the intra-articular distribution of the solution.

Histological Analysis

Five month after injection, the two knee joints from each animal were fixed for 36 to 48 hours in 10% buffered formalin then kept in 70% ethanol and followed by decalcification in 15% EDTA in phosphate buffer. Paraffin sections (3-4 µm) of the central region of the joint were stained with haematoxylin and eosin for histological analyses of cartilage structure, namely: loss of cartilage matrix, cellular abnormalities, appearance of articular cartilage mineralization front, formation of osteophytes and synovial membrane (microscopy: Nikon 80i). A semi-quantitative modified Mankin histological grading system was used to evaluate OA severity (Kraus et al., The OARSI histopathology initiative recommendations for histological assessments of osteoarthritis in the Guinea Pig. Osteoarthritis Cartilage, 2010 (18 S3) S35-S52). The articular cartilage area was analyzed quantitatively by immunohistochemistry (Pastoureau et al., Cartilage, bone and synovial histomorphometry in animal models of osteoarthritis. Osteoarthritis Cartilage. 2010 October; 18 Suppl 3:S106-12). Sections of guinea pig knees were stained with monoclonal antibody (monoclonal anti-chicken mouse collagen II, 6B3 clone—reference MAB887/250, Millipore). The measurement of the total area of articular cartilage was performed with Color deconvolution H DAB and Siox and the measurement of joint height by ImageJ ("Fit Ellipse" module). Statistical analyzes of scoring and quantification results were performed using a Kruskal-Wallis test followed by Dunn's test using PRISM software.

Results

Various histomorphometric parameters are then introduced, all of them expressing the OA pathology at the cartilage, bone and synovium levels. The greatest severity of both cartilage structural damage and loss of proteoglycan was evident for the medial tibial surface of the knee.

Results are shown in FIG. 1.

Comparing "sham" and "HA" groups, there were no significant differences in cartilage structure scoring as well proteoglycan and type II Collagen content, although the thickness of cartilage is highest for HA group.

Comparing the "peptide" group to "sham" and "HA", it was found in animals injected with the peptide of the invention a lowest severity of both cartilage structural damage and proteoglycan loss onto the medial tibial surface of the knee, as well as a decreased osteophytes scoring. Finally, the total scoring of degradation parameters are lowest for knee articulation of animals injected with the peptide of the invention. Moreover, in the guinea pigs administered with the peptide of the invention, there is a more sustained staining which highlights greater synthesis of type II collagen and an increase in the thickness of the cartilage. In resume, animals injected with a peptide of the invention have a highest thickness and a better cartilage quality than sham and HA injected animals.

Example 2: Stability of the Peptide of the Invention

Sample Preparation

Peptide alone, at a concentration of 0.9 mM (2.5 mg/ml), was dissolved in a Millipore filter treated water. Peptide+HA solution consists of peptide dissolved at 0.9 mM in a solution of HA (1.8 MDa) at 1% (10 mg/ml) in water.

Raman Scattering Measurements

Samples were placed in a suprasil quartz cell (5 mm path length) and excited by the 488 nm line of an Ar+ laser (Spectra Physics, CA, USA) with a ~200 mW power at the sample. Scattered light at right angle was analyzed on a Jobin-Yvon T64000 (HORIBA Jobin-Yvon, France) in a single spectrograph configuration with a 1200 grooves per mm holographic grating and a holographic notch filter. Stokes Raman data were collected by means of a liquid nitrogen cooled CCD detection system (Spectrum One, Jobin-Yvon, France). The effective spectral slit width was set to ~5 $cm^{-1}$. Each recorded spectrum corresponds to a total acquisition time of 1200 s. Buffer subtraction and smoothing of the observed Raman spectra could be performed using the GRAMS/AI package (Thermoage Galactic, MA, USA). The final presentation of these spectra was performed by means of SigmaPlot package (Systat Software Inc., CA, USA).

Results

Figure 2:
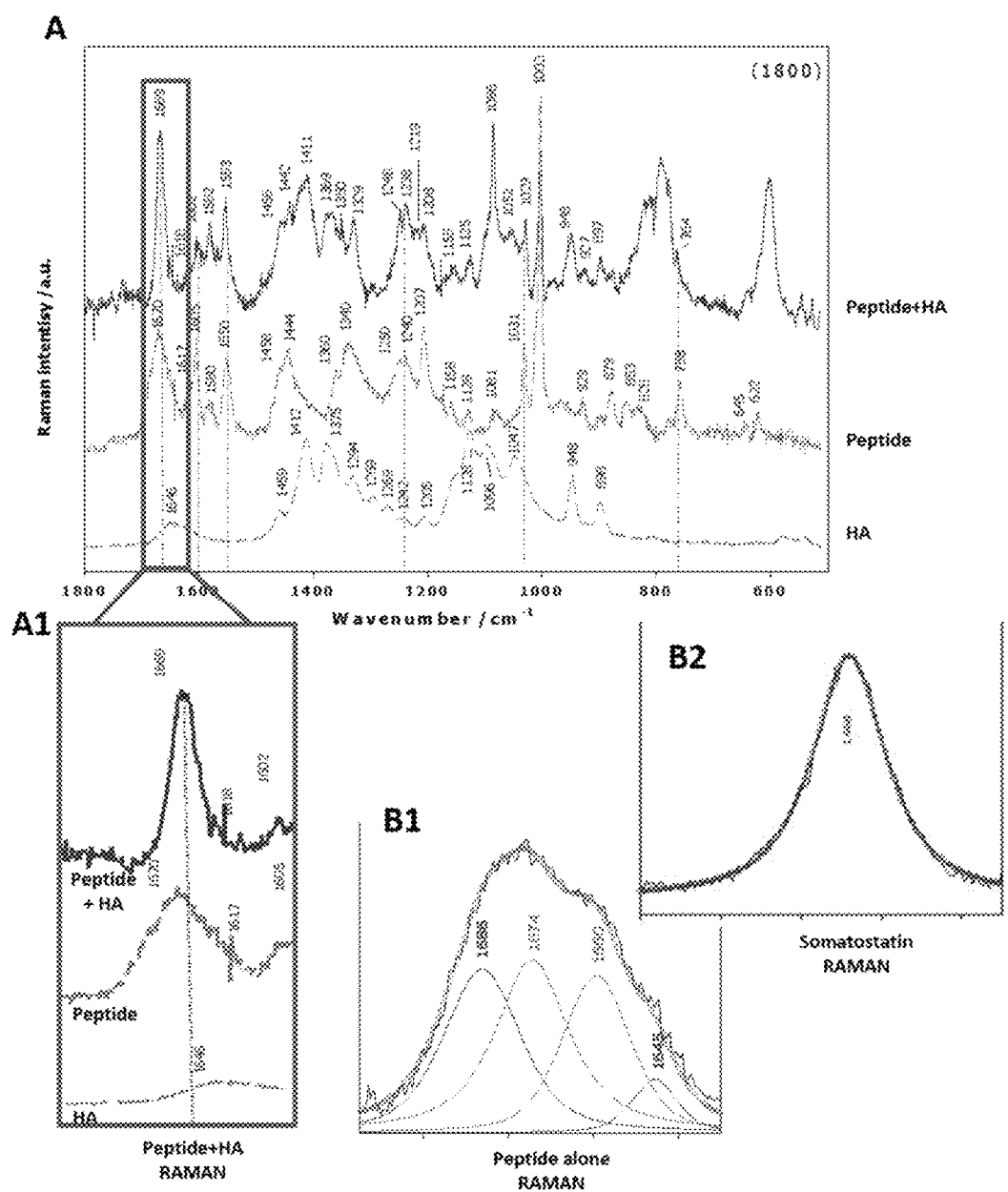
FIG. 2 is a Raman spectra showing the stabilization of peptide with sequence set forth as SEQ ID NO: 4 ("peptide") in presence of hyaluronic acid. Peptides described herein differ from endogenous somatostatin or from peptides known in the art and exhibit a β-hairpin molecular conformation which stability depends of physiological medium and hydrophobic medium used. This figure illustrates the Raman data obtained for peptide with sequence set forth as SEQ ID NO: 4 alone, hyaluronic acid alone and a mix of peptide with sequence set forth as SEQ ID NO: 4 and hyaluronic acid. Peptide with sequence set forth as SEQ ID NO: 4 has an unstable structure in water, reflected by the presence of four different conformations among which, three are quantitatively equivalent; whereas peptide with sequence set forth as SEQ ID NO: 4 together with hyaluronic acid has a stabilized β-hairpin conformation. This conformation may allow somatostatin residues to be exposed for their specific and high-affinity binding to their receptors.

Results are shown in FIG. 2.

FIG. 2A shows a Raman spectra, obtained from the aqueous solution of a mix with peptide and hyaluronic acid (HA). Peptide spectra are distinct of HA spectra. The beta-marker Raman band at 1669 $cm^{-1}$ is the major component observed in this region and assigned to H-bonded beta-strands of peptide.

FIG. 2A1 shows a focus on the spectral region 1646 $cm^{-1}$ of the Raman spectra recorded at 0.9 mM peptide—1% HA in water. It is observed the secondary peptide conformation belonging to the antiparallel beta sheet structure of the peptide.

FIG. 2B1 shows a decomposition of the Raman spectra of peptide alone observed in the spectral region between 1686 and 1645. Several (4) secondary conformations of peptide belonging to beta-form structures can be evidenced by band decomposition beta-strand residues implying the presence of inter-strand hydrogen bonds (marker at ca. 1660 $cm^{-1}$) and antiparallel beta sheet (a doublet in the frequency intervals at ca. 1686-1674 $cm^{-1}$ and one at ca. 1645 $cm^{-1}$.

FIG. 2B2 shows a schematic result of Raman spectra of somatostatin in phosphate buffer. The existence of the beta-marker Raman band at 1668 cm$^{-1}$ as the unique component observed in this region and assigned to H-bonded beta-strand.

Therefore, unlike the conformations adopted by the peptide alone in water (4 major bands), peptide HA kept a single secondary conformation as the beta sheet conformation of typical somatostatin.

Example 3: Effect of the Peptide of the Invention on the Osteoarticular Cartilage Quality and Quantity Sample Preparation Peptide of the invention (corresponding to SEQ ID NO: 4) was dissolved at 74.6 µg/ml in a solution of NaCl 0.9% containing 1% (10 mg/ml) of hyaluronic acid.

Animal IA Injection

The study was performed on males New-Zealand rabbits. Osteoarthritis is induced through the surgical transection of the anterior cruciate ligament of the right knee joint (this animal model, named ACLT model, is a well validated model of traumatic osteoarthritis). Ten 28-weeks old animals were injected per group. Rabbits were transected by ACLT of the right knee joint. 300 µl of the mix peptide of the invention/HA ("Peptide+HA group", corresponding to a peptide concentration within the joint after injection of about 10$^{-5}$M) or saline solution ("Control" group) or a commercially available hyaluronic acid having a molecular weight of 600 kDa (HA600, "HA" group) were administered through intra-articular injection into the right knee after total recovery from ACLT surgery (i.e. 14 days), repeated 3 times one week apart. Animals were euthanized 8 weeks after ACLT surgery.

Macroscopic Evaluation of Articular Structure

A macroscopic evaluation was performed on the four compartments of the joint: medial and lateral femoral condyles and medial and lateral tibial plateaus. Each lesion was evaluated for its grade (severity, score ranging from 0 to 4) and its size (score ranging from 0 to 7). The global macroscopic score corresponds to the sum of the score obtained for all the lesions in all compartments of the joint. The score can be considered as size×grade or size and grade separately. The four compartments are considered independent for the purpose of statistical analysis.

Results

The global macroscopic score (size×grade) in the whole population and in the low subpopulation (with the less severe lesions) of each group was analyzed. In the whole population, the administration of the combination of the peptide of the invention with hyaluronic acid leads to a decrease of the severity of the lesions as well as of the size of the lesion, whereas HA alone did not show any effect.

Figure 3:
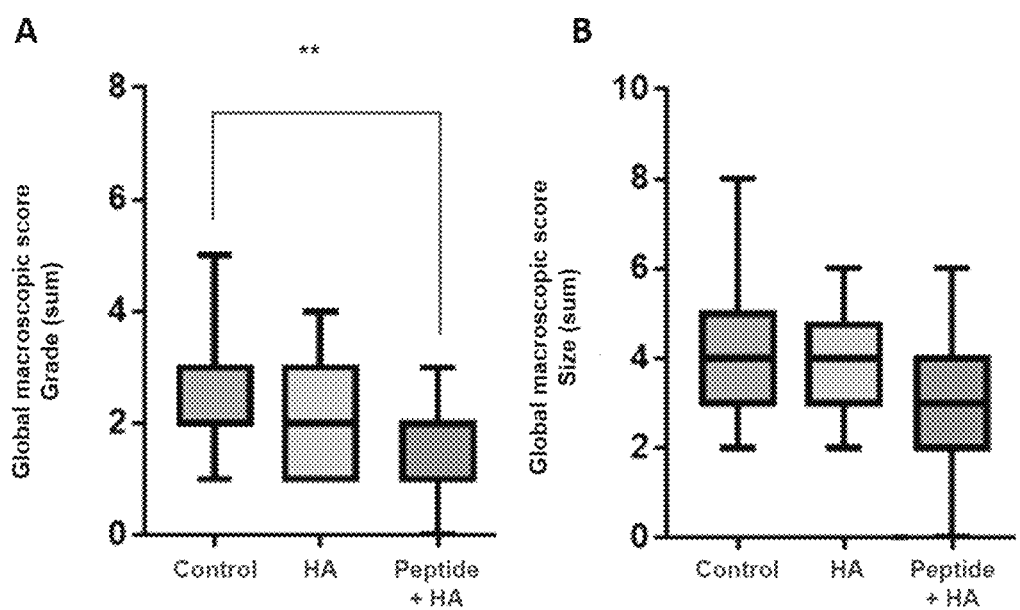
FIG. 3 is a graph showing in vivo efficiency tests carried out in rabbits for hyaluronic acid ("HA") versus peptide with sequence set forth as SEQ ID NO: 4 combined with HA ("peptide+HA"). (A) the histogram illustrates the sum of the global macroscopic score grade representing the lesion severity on macroscopic aspect for the low score subpopulation (animals with the less severe lesions). It shows a significant decrease of the score grade in presence of the peptide with sequence set forth as SEQ ID NO: 4 combined with HA as compared to both control and hyaluronic acid (HA) alone. (B) the histogram shows a decrease of the sum of the global macroscopic score size in presence of the peptide with sequence set forth as SEQ ID NO: 4. **=p-value<0.01.

In the low subpopulation of rabbit, there was no significant differences in the global macroscopic scores grade and size in "Control" and "HA" groups. However, comparing the "peptide+HA" group to "control" and "HA" groups, it was found in animals injected with the peptide of the invention combined with HA a significant decrease of the global macroscopic score grade (FIG. 3A). Moreover, in rabbits administered with the peptide of the invention combined with HA, it was also found a slight decrease of the global macroscopic score size, close to zero for some animals (FIG. 3B).

These results thus demonstrate the therapeutic potential of the combination of a peptide of the invention and hyaluronic acid in a model of traumatic osteoarthritis.

Example 4: Effect of the Combination of Peptides of the Invention and Hyaluronic Acid on Chondrogenesis Material and Methods Normal human articular chondrocytes from knee (NHAC-kn) were seeded into a culture chamber (8 wells) at 0.22×10$^6$ cells per well. NHAC-kn cells were expanded using the Chondrocyte Growth Medium containing fetal bovine serum 5%, gentamicin/amphotericin-B 0.1%, human recombinant Fibroblast Growth Factor-beta 0.5%, R3-Insulin-like Growth Factor-1 0.2%, insulin 0.2%, transferrin 0.1% in the presence of peptides of the invention with or without hyaluronic acid (HA) at a concentration of 10 µM. Medium was changed every 2 days. After 4 days of incubation, cells were fixed with formaldehyde and stained with alcian blue.

Results

The alcian blue staining revealed an increase of cell clusters for cells treated with the tested peptides alone indicating a stimulation of the chondrogenesis. The addition of hyaluronic acid induces a slight increase in cell proliferation, but no cluster formation. The addition of hyaluronic acid (HA) in combination with the peptide as set forth in SEQ ID NO: 2 induced more proliferation with a later effect on cluster formation than the peptide alone. Thus, the addition of hyaluronic acid in combination with the peptide allowed a better proliferation of cells and a better long term effect than the peptides tested alone.

SEQUENCE LISTING

```
<160> NUMBER OF SEQ ID NOS: 20

<210> SEQ ID NO 1
<211> LENGTH: 38
<212> TYPE: PRT
<213> ORGANISM: Artificial Sequence
<220> FEATURE:
<221> NAME/KEY: SITE
<222> LOCATION: 1
<223> OTHER INFORMATION: X is either vacant or G, with the proviso that
      X is perforce vacant if X in position 2 is vacant or G; and with
      the proviso that X is perforce vacant or G if X in position 2 is A
<220> FEATURE:
<223> OTHER INFORMATION: Chimeric peptide
<220> FEATURE:
<221> NAME/KEY: SITE
<222> LOCATION: 2
<223> OTHER INFORMATION: X is either vacant, A or G, with the proviso
```

```
            that X is perforce vacant if X in position 3 is vacant; and with
            the proviso that X is perforce vacant or G if X in position 3 is
            T; and with the proviso that X is perforce vacant or A if X in
            position 3 is S
<220> FEATURE:
<221> NAME/KEY: SITE
<222> LOCATION: 3
<223> OTHER INFORMATION: X is either vacant, S or T, with the proviso
            that X is perforce vacant if X in position 4 is vacant; and
            with the proviso that X is perforce vacant or S if X in position
            4 is D; and with the proviso that X is perforce vacant or T if X
            in position 4 is S
<220> FEATURE:
<221> NAME/KEY: SITE
<222> LOCATION: 4
<223> OTHER INFORMATION: X is either vacant, S or D; with the proviso
            that X is perforce vacant if X in position 5 is vacant; and with
            the proviso that X is perforce S or vacant if X in position 5 is
            D; and with the proviso that X is perforce D or vacant if X in
            position 5 is S
<220> FEATURE:
<221> NAME/KEY: SITE
<222> LOCATION: 5
<223> OTHER INFORMATION: X is either vacant, D or S; with the proviso
            that X is perforce vacant if X in position 6 is vacant; and with
            the proviso that X is perforce S if X in position 6 is D or N; and
            with the proviso that X is perforce vacant or D if X in position
            6 is R
<220> FEATURE:
<221> NAME/KEY: SITE
<222> LOCATION: 6
<223> OTHER INFORMATION: X is either vacant, N, D or R; with the proviso
            that X is perforce vacant if X in position 7 is vacant
<220> FEATURE:
<221> NAME/KEY: SITE
<222> LOCATION: 7
<223> OTHER INFORMATION: X is either vacant or V
<220> FEATURE:
<221> NAME/KEY: SITE
<222> LOCATION: 9
<223> OTHER INFORMATION: X is E or D
<220> FEATURE:
<221> NAME/KEY: SITE
<222> LOCATION: 10
<223> OTHER INFORMATION: X is K or S if X in position 9 is E; or X is L
            if X in position 9 is D
<220> FEATURE:
<221> NAME/KEY: SITE
<222> LOCATION: 12
<223> OTHER INFORMATION: X is either vacant or K
<220> FEATURE:
<221> NAME/KEY: SITE
<222> LOCATION: 13
<223> OTHER INFORMATION: X is either vacant or D; with the proviso that
            X is perforce vacant if X at position 12 is also vacant
<220> FEATURE:
<221> NAME/KEY: SITE
<222> LOCATION: 14
<223> OTHER INFORMATION: X is either vacant or L; with the proviso that
            X is perforce vacant if X at position 13 is also vacant
<220> FEATURE:
<221> NAME/KEY: SITE
<222> LOCATION: 15
<223> OTHER INFORMATION: X is either vacant or E; with the proviso that
            X is perforce vacant if X at position 14 is also vacant
<220> FEATURE:
<221> NAME/KEY: SITE
<222> LOCATION: 16
<223> OTHER INFORMATION: X is either vacant or E; with the proviso that
            X is perforce vacant if X at position 15 is also vacant
<220> FEATURE:
<221> NAME/KEY: SITE
<222> LOCATION: 17
<223> OTHER INFORMATION: X is either vacant or G; with the proviso that
            X is perforce vacant if X at position 16 is also vacant
<220> FEATURE:
<221> NAME/KEY: SITE
<222> LOCATION: 18
<223> OTHER INFORMATION: X is either vacant or I; with the proviso that
```

X is perforce vacant if X at position 17 is also vacant
<220> FEATURE:
<221> NAME/KEY: SITE
<222> LOCATION: 19
<223> OTHER INFORMATION: X is either vacant or Q; with the proviso that
X is perforce vacant if X at position 18 is also vacant
<220> FEATURE:
<221> NAME/KEY: SITE
<222> LOCATION: 20
<223> OTHER INFORMATION: X is either vacant, A or T; with the proviso
that X is perforce vacant if X at position 19 is also vacant
<220> FEATURE:
<221> NAME/KEY: SITE
<222> LOCATION: 21
<223> OTHER INFORMATION: X is either vacant or L; with the proviso
that X is perforce vacant if X at position 20 is also vacant
<220> FEATURE:
<221> NAME/KEY: SITE
<222> LOCATION: 24
<223> OTHER INFORMATION: X is either C, S, Y, F, D, E, A or G
<220> FEATURE:
<221> NAME/KEY: SITE
<222> LOCATION: 29
<223> OTHER INFORMATION: X is either vacant or W
<220> FEATURE:
<221> NAME/KEY: SITE
<222> LOCATION: 30
<223> OTHER INFORMATION: X is either vacant or K; with the proviso that
X is perforce vacant if X at position 29 is also vacant
<220> FEATURE:
<221> NAME/KEY: SITE
<222> LOCATION: 31
<223> OTHER INFORMATION: X is either vacant or T; with the proviso that
X is perforce vacant if X at position 30 is also vacant
<220> FEATURE:
<221> NAME/KEY: SITE
<222> LOCATION: 32
<223> OTHER INFORMATION: X is either vacant or F; with the proviso that
X is perforce vacant if X at position 31 is also vacant
<220> FEATURE:
<221> NAME/KEY: SITE
<222> LOCATION: 33
<223> OTHER INFORMATION: X is either vacant or T; with the proviso that
X is perforce vacant if X at position 32 is also vacant
<220> FEATURE:
<221> NAME/KEY: SITE
<222> LOCATION: 34
<223> OTHER INFORMATION: X is either vacant or S; with the proviso that
X is perforce vacant if X at position 33 is also vacant
<220> FEATURE:
<221> NAME/KEY: SITE
<222> LOCATION: 35
<223> OTHER INFORMATION: X is either vacant, C, S, Y, F, D, E, A or G;
with the proviso that X is perforce vacant if X at position 34 is
also vacant
<220> FEATURE:
<221> NAME/KEY: SITE
<222> LOCATION: 36
<223> OTHER INFORMATION: X is either vacant or K; with the proviso that
X is perforce vacant if X at position 35 is also vacant
<220> FEATURE:
<221> NAME/KEY: SITE
<222> LOCATION: 37
<223> OTHER INFORMATION: X is either vacant or Q; with the proviso that
X is perforce vacant if X at position 36 is also vacant; and with
the proviso that X is perforce Q if X at position 36 is K
<220> FEATURE:
<221> NAME/KEY: SITE
<222> LOCATION: 38
<223> OTHER INFORMATION: X is either vacant or A; with the proviso that
X is perforce vacant if X at position 37 is also vacant; and with
the proviso that X is perforce A if X at position 37 is Q

<400> SEQUENCE: 1

Xaa Xaa Xaa Xaa Xaa Xaa Xaa Tyr Xaa Xaa Leu Xaa Xaa Xaa Xaa Xaa
1               5                   10                  15

Xaa Xaa Xaa Xaa Xaa Ala Gly Xaa Lys Asn Phe Phe Xaa Xaa Xaa Xaa

```
                   20                  25                  30

Xaa Xaa Xaa Xaa Xaa Xaa
            35

<210> SEQ ID NO 2
<211> LENGTH: 25
<212> TYPE: PRT
<213> ORGANISM: Artificial Sequence
<220> FEATURE:
<223> OTHER INFORMATION: Chimeric peptide

<400> SEQUENCE: 2

Gly Ala Ser Asp Ser Asp Val Tyr Asp Leu Leu Ala Gly Ser Lys Asn
1               5                   10                  15

Phe Phe Trp Lys Thr Phe Thr Ser Ser
            20                  25

<210> SEQ ID NO 3
<211> LENGTH: 26
<212> TYPE: PRT
<213> ORGANISM: Artificial Sequence
<220> FEATURE:
<223> OTHER INFORMATION: Chimeric peptide

<400> SEQUENCE: 3

Gly Ala Ser Asp Ser Asp Val Tyr Asp Leu Leu Lys Ala Gly Ser Lys
1               5                   10                  15

Asn Phe Phe Trp Lys Thr Phe Thr Ser Ser
            20                  25

<210> SEQ ID NO 4
<211> LENGTH: 24
<212> TYPE: PRT
<213> ORGANISM: Artificial Sequence
<220> FEATURE:
<223> OTHER INFORMATION: Chimeric peptide

<400> SEQUENCE: 4

Gly Thr Ser Asp Arg Val Tyr Glu Lys Leu Ala Gly Ser Lys Asn Phe
1               5                   10                  15

Phe Trp Lys Thr Phe Thr Ser Ser
            20

<210> SEQ ID NO 5
<211> LENGTH: 5
<212> TYPE: PRT
<213> ORGANISM: Artificial Sequence
<220> FEATURE:
<223> OTHER INFORMATION: Positions 3-7 of chimeric peptide
<220> FEATURE:
<221> NAME/KEY: SITE
<222> LOCATION: 3
<223> OTHER INFORMATION: X is either R or S
<220> FEATURE:
<221> NAME/KEY: SITE
<222> LOCATION: 4
<223> OTHER INFORMATION: X is either vacant, D or N; with the proviso
      that X is vacant if X in position 3 is R; and with the proviso
      that X is D or N if X in position 3 is S

<400> SEQUENCE: 5

Ser Asp Xaa Xaa Val
1               5

<210> SEQ ID NO 6
<211> LENGTH: 6
```

```
<212> TYPE: PRT
<213> ORGANISM: Artificial Sequence
<220> FEATURE:
<221> NAME/KEY: SITE
<222> LOCATION: 1
<223> OTHER INFORMATION: X is either T or A; with the proviso that X is
      T if X in position 4 is R; and with the proviso that X is A if X
      in position 4 is S
<220> FEATURE:
<223> OTHER INFORMATION: Positions 2-7 of chimeric peptide
<220> FEATURE:
<221> NAME/KEY: SITE
<222> LOCATION: 4
<223> OTHER INFORMATION: X is either R or S
<220> FEATURE:
<221> NAME/KEY: SITE
<222> LOCATION: 5
<223> OTHER INFORMATION: X is either vacant, D or N; with the proviso
      that X is vacant if X in position 4 is R; and with the proviso
      that X is D or N if X in position 4 is S

<400> SEQUENCE: 6

Xaa Ser Asp Xaa Xaa Val
1               5

<210> SEQ ID NO 7
<211> LENGTH: 7
<212> TYPE: PRT
<213> ORGANISM: Artificial Sequence
<220> FEATURE:
<223> OTHER INFORMATION: Positions 1-7 of chimeric peptide
<220> FEATURE:
<221> NAME/KEY: SITE
<222> LOCATION: 2
<223> OTHER INFORMATION: X is either T or A; with the proviso that X is
      T if X in position 5 is R; and with the proviso that X is A if X
      in position 5 is S
<220> FEATURE:
<221> NAME/KEY: SITE
<222> LOCATION: 5
<223> OTHER INFORMATION: X is either R or S
<220> FEATURE:
<221> NAME/KEY: SITE
<222> LOCATION: 6
<223> OTHER INFORMATION: X is either vacant, D or N; with the proviso
      that X is vacant if X in position 5 is R; and with the proviso
      that X is D or N if X in position 5 is S

<400> SEQUENCE: 7

Gly Xaa Ser Asp Xaa Xaa Val
1               5

<210> SEQ ID NO 8
<211> LENGTH: 4
<212> TYPE: PRT
<213> ORGANISM: Artificial Sequence
<220> FEATURE:
<223> OTHER INFORMATION: Positions 12-15 of chimeric peptide

<400> SEQUENCE: 8

Lys Asp Leu Glu
1

<210> SEQ ID NO 9
<211> LENGTH: 5
<212> TYPE: PRT
<213> ORGANISM: Artificial Sequence
<220> FEATURE:
<223> OTHER INFORMATION: Positions 12-16 of chimeric peptide

<400> SEQUENCE: 9

Lys Asp Leu Glu Glu
```

<210> SEQ ID NO 10
<211> LENGTH: 6
<212> TYPE: PRT
<213> ORGANISM: Artificial Sequence
<220> FEATURE:
<223> OTHER INFORMATION: Positions 12-17 of chimeric peptide

<400> SEQUENCE: 10

Lys Asp Leu Glu Glu Gly
1               5

<210> SEQ ID NO 11
<211> LENGTH: 7
<212> TYPE: PRT
<213> ORGANISM: Artificial Sequence
<220> FEATURE:
<223> OTHER INFORMATION: Positions 12-18 of chimeric peptide

<400> SEQUENCE: 11

Lys Asp Leu Glu Glu Gly Ile
1               5

<210> SEQ ID NO 12
<211> LENGTH: 8
<212> TYPE: PRT
<213> ORGANISM: Artificial Sequence
<220> FEATURE:
<223> OTHER INFORMATION: Positions 12-19 of chimeric peptide

<400> SEQUENCE: 12

Lys Asp Leu Glu Glu Gly Ile Gln
1               5

<210> SEQ ID NO 13
<211> LENGTH: 9
<212> TYPE: PRT
<213> ORGANISM: Artificial Sequence
<220> FEATURE:
<223> OTHER INFORMATION: Positions 12-20 of chimeric peptide
<220> FEATURE:
<221> NAME/KEY: SITE
<222> LOCATION: 9
<223> OTHER INFORMATION: X is A or T

<400> SEQUENCE: 13

Lys Asp Leu Glu Glu Gly Ile Gln Xaa
1               5

<210> SEQ ID NO 14
<211> LENGTH: 10
<212> TYPE: PRT
<213> ORGANISM: Artificial Sequence
<220> FEATURE:
<223> OTHER INFORMATION: Positions 12-21 of chimeric peptide
<220> FEATURE:
<221> NAME/KEY: SITE
<222> LOCATION: 9
<223> OTHER INFORMATION: X is A or T

<400> SEQUENCE: 14

Lys Asp Leu Glu Glu Gly Ile Gln Xaa Leu
1               5                   10

<210> SEQ ID NO 15
<211> LENGTH: 4
<212> TYPE: PRT

```
<213> ORGANISM: Artificial Sequence
<220> FEATURE:
<223> OTHER INFORMATION: Positions 29-32 of chimeric peptide

<400> SEQUENCE: 15

Trp Lys Thr Phe
1

<210> SEQ ID NO 16
<211> LENGTH: 5
<212> TYPE: PRT
<213> ORGANISM: Artificial Sequence
<220> FEATURE:
<223> OTHER INFORMATION: Positions 29-33 of chimeric peptide

<400> SEQUENCE: 16

Trp Lys Thr Phe Thr
1               5

<210> SEQ ID NO 17
<211> LENGTH: 6
<212> TYPE: PRT
<213> ORGANISM: Artificial Sequence
<220> FEATURE:
<223> OTHER INFORMATION: Positions 29-34 of chimeric peptide

<400> SEQUENCE: 17

Trp Lys Thr Phe Thr Ser
1               5

<210> SEQ ID NO 18
<211> LENGTH: 7
<212> TYPE: PRT
<213> ORGANISM: Artificial Sequence
<220> FEATURE:
<223> OTHER INFORMATION: Positions 29-35 of chimeric peptide
<220> FEATURE:
<221> NAME/KEY: SITE
<222> LOCATION: 7
<223> OTHER INFORMATION: X is either of C, S, Y, F, D, E, A or G

<400> SEQUENCE: 18

Trp Lys Thr Phe Thr Ser Xaa
1               5

<210> SEQ ID NO 19
<211> LENGTH: 10
<212> TYPE: PRT
<213> ORGANISM: Artificial Sequence
<220> FEATURE:
<223> OTHER INFORMATION: Positions 29-38 of chimeric peptide
<220> FEATURE:
<221> NAME/KEY: SITE
<222> LOCATION: 7
<223> OTHER INFORMATION: X is either of C, S, Y, F, D, E, A or G

<400> SEQUENCE: 19

Trp Lys Thr Phe Thr Ser Xaa Lys Gln Ala
1               5                   10

<210> SEQ ID NO 20
<211> LENGTH: 26
<212> TYPE: PRT
<213> ORGANISM: Artificial Sequence
<220> FEATURE:
<223> OTHER INFORMATION: Chimeric peptide

<400> SEQUENCE: 20
```

```
Gly Ala Ser Asp Ser Asn Val Tyr Asp Leu Leu Lys Ala Gly Ser Lys
1               5                   10                  15

Asn Phe Phe Trp Lys Thr Phe Thr Ser Ser
                20              25
```

The invention claimed is:

1. A method for treating osteoarthritis in a subject in need thereof, comprising administering to the subject a peptide comprising an amino acid sequence SEQ ID NO: 1, or a or variant thereof, said variant being a peptide showing at least 95% identity with SEQ ID NO: 1, wherein SEQ ID NO: 1 is the following:

```
                                            (SEQ ID NO: 1)
X1-Tyr-X2-Leu-X3-Ala-Gly-X4-Lys-Asn-Phe-Phe-X5
``` wherein:
- $X_1$ is Gly-$Z_2$-Ser-Asp-$Z_1$-Val (SEQ ID NO: 7); wherein $Z_1$ is arginine and $Z_2$ threonine, or $Z_1$ is Ser-Asp or Ser-Asn and $Z_2$ is alanine;
- $X_2$ is a sequence selected from Glu-Lys, Glu-Ser and Asp-Leu;
- $X_3$ is vacant or is lysine;
- $X_4$ is an amino acid residue selected from cysteine, serine, tyrosine, phenylalanine, aspartic acid, glutamic acid, alanine and glycine; and
- $X_5$ is Trp-Lys-Thr-Phe-Thr-Ser-$X_6$ (SEQ ID NO: 18); wherein $X_6$ is an amino acid residue selected from cysteine, serine, tyrosine, phenylalanine, aspartic acid, glutamic acid, alanine and glycine.

2. The method according to claim 1, wherein the peptide consists in an amino acid sequence ranging from 20 to 30 amino acid residues.

3. The method according to claim 1, wherein the peptide comprises a sequence SEQ ID NO: 2, 3, 4 or 20 or a variant thereof, said variant being a peptide showing at least 95% identity with SEQ ID NO: 2, 3, 4 or 20:

```
                                            (SEQ ID NO: 2)
Gly-Ala-Ser-Asp-Ser-Asp-Val-Tyr-Asp-Leu-Leu-
Ala-Gly-Ser-Lys-Asn-Phe-Phe-Trp-Lys-Thr-Phe-
Thr-Ser-Ser (SEQ ID NO: 3)
Gly-Ala-Ser-Asp-Ser-Asp-Val-Tyr-Asp-Leu-Leu-
Lys-Ala-Gly-Ser-Lys-Asn-Phe-Phe-Trp-Lys-Thr-
Phe-Thr-Ser-Ser (SEQ ID NO: 4)
Gly-Thr-Ser-Asp-Arg-Val-Tyr-Glu-Lys-Leu-Ala-
Gly-Ser-Lys-Asn-Phe-Phe-Trp-Lys-Thr-Phe-Thr-
Ser-Ser (SEQ ID NO: 20)
Gly-Ala-Ser-Asp-Ser-Asn-Val-Tyr-Asp-Leu-Leu-
Lys-Ala-Gly-Ser-Lys-Asn-Phe-Phe-Trp-Lys-Thr-
Phe-Thr-Ser-Ser.
```

4. The method according to claim 1, wherein said peptide is administered to the subject by intra-articular injection in the joint to be treated.

5. The method according to claim 1, wherein said peptide is administered at a final concentration in the joint ranging from $10^{-3}$M to $10^{-7}$ M.

6. The method according to claim 1, wherein said peptide is comprised within a pharmaceutical composition containing one or more pharmaceutically acceptable excipients.

7. The method according to claim 1, wherein said peptide is comprised within a medicament.

8. The method according to claim 1, wherein said peptide is comprised within a pharmaceutical unit dosage form.

9. The method according to claim 8, wherein the unit dosage form is a single-use pre-filled, pre-dosed syringe for local injection in the joint to be treated.

10. The method according to claim 1, wherein said peptide is administered with at least one viscosupplementation agent.

11. The method according to claim 1, wherein said peptide is administered with hyaluronic acid.

12. The method according to claim 11, wherein said hyaluronic acid is at a concentration ranging from 0.1% to 10%.

13. The method according to claim 1, wherein the subject is affected by grade 0, 1 or 2 osteoarthritis according to the Kellgren-Lawrence grade (or K-L system).

14. The method according to claim 1, wherein the subject is affected by grade 0, 1, 2 or 3 osteoarthritis according to the Kellgren-Lawrence grade (or K-L system).

* * * * *